US006296622B1

(12) United States Patent
Kurz et al.

(10) Patent No.: US 6,296,622 B1
(45) Date of Patent: *Oct. 2, 2001

(54) ENDOLUMINAL DEVICE DELIVERY SYSTEM USING AXIALLY RECOVERING SHAPE MEMORY MATERIAL

(75) Inventors: Daniel R. Kurz, Sunnyvale; Rose Y. Wong; Crystal K. Sein-Lwyn, both of Hayward; David A. Ferrera, San Francisco; Lok A. Lei, San Jose; Nicholas C. Debeer, San Francisco, all of CA (US)

(73) Assignee: Micrus Corporation, Mountain View, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/218,117

(22) Filed: Dec. 21, 1998

(51) Int. Cl.$^7$ .......................... A61M 11/00; A61M 29/00
(52) U.S. Cl. .................. 604/93.01; 606/191; 606/198
(58) Field of Search .................. 604/93.01, 95.05, 604/164.03, 164.13, 530, 531; 623/1.11, 1.12, 1.23; 606/209, 194, 191, 198, 151, 108

(56) References Cited

U.S. PATENT DOCUMENTS

| Re. 32,348 | 2/1987 | Pevsner . |
| 1,341,052 | 5/1920 | Gale . |
| 2,078,182 | 4/1937 | MacFarland . |

(List continued on next page.)

FOREIGN PATENT DOCUMENTS

| 4102550 A1 | 8/1991 | (DE) . |
| 0 183 372 A1 | 6/1986 | (EP) . |

(List continued on next page.)

OTHER PUBLICATIONS

"Retrievable Gianturco–Coil Introducer" by Jeffrey Hawkins, Ronald G. Quisling, MD, J. Parker Mickle, MD, Irvin F. Hawkins, MD from the Departments of Radiology and Neurosurgery (J.P.M.) University of Florida Medical Center (1986).

(List continued on next page.)

*Primary Examiner*—Richard K. Seidel
*Assistant Examiner*—Michael J Hayes
(74) *Attorney, Agent, or Firm*—Fulwider Patton Lee & Utecht, LLP

(57) ABSTRACT

The endoluminal device delivery system and method for delivering an endoluminal device within a body lumen uses shape memory material in the form of a tubular collar to engage the endoluminal device during delivery to the desired location. The endoluminal device is engaged internally within the tubular collar either mechanically by crimping the tubular collar around a portion of the endoluminal device, or through an adhesive bond. The tubular collar can be crimped about a rounded portion of the stem of the endoluminal device. Once the endoluminal device is maneuvered through the body lumens to the desired location, it is decoupled from the delivery system by applying heat to the tubular collar of shape memory material. When the tubular collar has been heated to a sufficient temperature, it will transition to a rubbery state and shrink in length, thereby retracting completely back on to the optical fiber, causing the distal end of the optical fiber to engage the endoluminal device and dislodge it from the tubular collar. An interlocking assembly can also be utilized at the stem portion of the endoluminal therapeutic device to releaseably connect the endoluminal therapeutic device to the elongated pusher member. The body of shape memory material can also be bonded to both the pusher member and the endoluminal device, with the tubular collar being scored to break when the tubular collar changes from the stressed configuration to the recovered configuration. A collet can also be mounted to the pusher member and disposed within.

22 Claims, 7 Drawing Sheets

U.S. PATENT DOCUMENTS

| | | |
|---|---|---|
| 2,549,335 | 4/1951 | Rahthus . |
| 3,334,629 | 8/1967 | Cohn . |
| 3,485,234 | 12/1969 | Stevens . |
| 3,649,224 | 3/1972 | Anderson et al. . |
| 3,868,956 | 3/1975 | Alfidi et al. . |
| 4,327,734 | 5/1982 | White, Jr. . |
| 4,341,218 | 7/1982 | Ü . |
| 4,346,712 | 8/1982 | Handa et al. . |
| 4,402,319 | 9/1983 | Handa et al. . |
| 4,441,495 * | 4/1984 | Hicswa ................................ 128/325 |
| 4,494,531 | 1/1985 | Gianturco . |
| 4,512,338 | 4/1985 | Balko et al. . |
| 4,545,367 | 10/1985 | Tucci . |
| 4,553,545 | 11/1985 | Maass et al. . |
| 4,611,594 | 9/1986 | Grayhack et al. . |
| 4,629,458 | 12/1986 | Pinchuk . |
| 4,638,803 | 1/1987 | Rand . |
| 4,655,771 | 4/1987 | Wallsten . |
| 4,670,286 | 6/1987 | Nyilas et al. . |
| 4,718,907 | 1/1988 | Karwoski et al. . |
| 4,732,152 | 3/1988 | Wallstén et al. . |
| 4,748,986 | 6/1988 | Morrison et al. . |
| 4,768,507 | 9/1988 | Fischell et al. . |
| 4,795,458 | 1/1989 | Regan . |
| 4,798,606 | 1/1989 | Pinchuk . |
| 4,800,882 | 1/1989 | Gianturco . |
| 4,813,925 | 3/1989 | Anderson, Jr. et al. . |
| 4,820,298 | 4/1989 | Leveen et al. . |
| 4,830,003 | 5/1989 | Wolff et al. . |
| 4,850,960 | 7/1989 | Grayzel . |
| 4,856,516 | 8/1989 | Hillstead . |
| 4,873,978 | 10/1989 | Ginsburg . |
| 4,950,258 | 8/1990 | Kawai et al. . |
| 4,954,126 | 9/1990 | Wallsten . |
| 4,957,051 | 9/1990 | Lahille et al. . |
| 4,957,479 | 9/1990 | Roemer . |
| 4,990,155 | 2/1991 | Wilkoff . |
| 4,994,069 | 2/1991 | Ritchart et al. . |
| 4,994,071 | 2/1991 | MacGregor . |
| 5,002,556 | 3/1991 | Ishida et al. . |
| 5,015,253 | 5/1991 | MacGregor . |
| 5,019,090 | 5/1991 | Pinchuk . |
| 5,026,377 | 6/1991 | Burton et al. . |
| 5,035,706 | 7/1991 | Giantureo et al. . |
| 5,037,377 | 8/1991 | Alonso . |
| 5,041,084 | 8/1991 | DeVries et al. . |
| 5,041,126 | 8/1991 | Gianturco . |
| 5,061,275 | 10/1991 | Wallstén et al. . |
| 5,064,435 | 11/1991 | Porter . |
| 5,071,407 | 12/1991 | Termin et al. . |
| 5,104,404 | 4/1992 | Wolff . |
| 5,108,407 | 4/1992 | Geremia et al. . |
| 5,109,867 | 5/1992 | Twyford, Jr. . |
| 5,122,136 | 6/1992 | Guglielmi et al. . |
| 5,133,364 | 7/1992 | Palermo et al. . |
| 5,133,731 | 7/1992 | Butler et al. . |
| 5,133,732 | 7/1992 | Wiktor . |
| 5,141,502 | 8/1992 | Macaluso, Jr. . |
| 5,143,085 | 9/1992 | Wilson . |
| 5,147,370 | 9/1992 | McNamara et al. . |
| 5,151,105 | 9/1992 | Kwan-Gett . |
| 5,152,784 | 10/1992 | Tsilibary . |
| 5,160,341 | 11/1992 | Brenneman et al. . |
| 5,171,273 | 12/1992 | Silver et al. . |
| 5,176,625 | 1/1993 | Brisson . |
| 5,176,661 | 1/1993 | Evard et al. . |
| 5,181,921 | 1/1993 | Makita et al. . |
| 5,183,085 | 2/1993 | Timmermans . |
| 5,186,992 | 2/1993 | Kite, III . |
| 5,188,621 | 2/1993 | Samson . |
| 5,192,290 | 3/1993 | Hilal . |
| 5,197,977 | 3/1993 | Hoffman, Jr. et al. . |
| 5,203,772 | 4/1993 | Hammerslag et al. . |
| 5,211,658 | 5/1993 | Clouse . |
| 5,217,484 | 6/1993 | Marks . |
| 5,222,969 | 6/1993 | Gillis . |
| 5,222,970 | 6/1993 | Reeves . |
| 5,224,953 | 7/1993 | Morgentaler . |
| 5,226,911 | 7/1993 | Chee et al. . |
| 5,226,913 | 7/1993 | Pinchuk . |
| 5,228,453 | 7/1993 | Sepetka . |
| 5,234,456 | 8/1993 | Silvestrini . |
| 5,238,004 | 8/1993 | Sahatjian et al. . |
| 5,250,071 | 10/1993 | Palermo . |
| 5,256,146 | 10/1993 | Ensminger et al. . |
| 5,258,042 | 11/1993 | Mehta . |
| 5,261,916 | 11/1993 | Engelson . |
| 5,275,173 | 1/1994 | Samson et al. . |
| 5,304,194 | 4/1994 | Chee et al. . |
| 5,312,415 | 5/1994 | Palermo . |
| 5,314,472 | 5/1994 | Fontaine . |
| 5,322,501 | 6/1994 | Mahmud-Durrani . |
| 5,336,205 | 8/1994 | Zenzen et al. . |
| 5,341,818 | 8/1994 | Abrams et al. . |
| 5,342,387 | 8/1994 | Summers . |
| 5,350,397 | 9/1994 | Palermo et al. . |
| 5,354,295 | 10/1994 | Guglielmi et al. . |
| 5,354,309 | 10/1994 | Schnepp-Pesch et al. . |
| 5,368,049 | 11/1994 | Raman et al. . |
| 5,373,856 | 12/1994 | Grenouillet . |
| 5,382,259 | 1/1995 | Phelps et al. . |
| 5,383,887 | 1/1995 | Nadal . |
| 5,395,390 | 3/1995 | Simon et al. . |
| 5,405,377 | 4/1995 | Cragg . |
| 5,409,015 | 4/1995 | Palermo . |
| 5,411,475 | 5/1995 | Atala et al. . |
| 5,413,597 | 5/1995 | Krajicek . |
| 5,415,664 | 5/1995 | Pinchuk . |
| 5,417,708 | 5/1995 | Hall et al. . |
| 5,423,829 | 6/1995 | Pham et al. . |
| 5,433,723 | 7/1995 | Lindenberg et al. . |
| 5,441,516 | 8/1995 | Wang et al. . |
| 5,443,478 | 8/1995 | Purdy . |
| 5,443,498 | 8/1995 | Fontaine . |
| 5,484,449 | 1/1996 | Amundson et al. . |
| 5,500,013 | 3/1996 | Buscemi et al. . |
| 5,514,115 | 5/1996 | Frantzen et al. . |
| 5,514,176 | 5/1996 | Bosley, Jr. . |
| 5,520,194 | 5/1996 | Miyata et al. . |
| 5,522,822 | 6/1996 | Phelps et al. . |
| 5,522,836 | 6/1996 | Palermo . |
| 5,523,092 | 6/1996 | Hanson et al. . |
| 5,527,336 | 6/1996 | Rosenbluth et al. . |
| 5,540,701 | 7/1996 | Sharkey et al. . |
| 5,549,624 | 8/1996 | Mirigian et al. . |
| 5,562,641 | 10/1996 | Flomenblit et al. . |
| 5,562,698 | 10/1996 | Parker . |
| 5,569,245 | 10/1996 | Guglielmi et al. . |
| 5,578,074 | 11/1996 | Mirigian . |
| 5,582,619 | 12/1996 | Ken . |
| 5,603,694 | 2/1997 | Brown et al. . |
| 5,607,445 | 3/1997 | Summers . |
| 5,609,627 | 3/1997 | Goicoechea et al. . |
| 5,613,981 | 3/1997 | Boyle et al. . |
| 5,624,461 | 4/1997 | Mariant . |
| 5,637,113 | 6/1997 | Tartaglia et al. . |
| 5,638,827 | 6/1997 | Palmer et al. . |
| 5,639,277 | 6/1997 | Mariant et al. . |
| 5,643,254 | 7/1997 | Scheldrup et al. . |
| 5,643,339 | 7/1997 | Kavteldaze et al. . |
| 5,645,564 | 7/1997 | Northrup et al. . |

| | | |
|---|---|---|
| 5,649,949 | 7/1997 | Wallace et al. . |
| 5,653,726 | 8/1997 | Kieturakis . |
| 5,653,727 | 8/1997 | Wiktor . |
| 5,666,968 | 9/1997 | Imran et al. . |
| 5,667,522 | 9/1997 | Flomenblit et al. . |
| 5,676,697 | 10/1997 | McDonald . |
| 5,690,643 | 11/1997 | Wijay . |
| 5,690,666 | 11/1997 | Berenstein et al. . |
| 5,690,671 | 11/1997 | McGurk et al. . |
| 5,693,085 | 12/1997 | Buirge et al. . |
| 5,702,373 | 12/1997 | Samson . |
| 5,702,414 | 12/1997 | Richter et al. . |
| 5,713,907 | 2/1998 | Hogendijk et al. . |
| 5,722,989 | 3/1998 | Fitch et al. . |
| 5,725,546 | 3/1998 | Samson . |
| 5,733,329 | 3/1998 | Wallace et al. . |
| 5,743,905 | 4/1998 | Eder et al. . |
| 5,746,765 | 5/1998 | Kleshinski et al. . |
| 5,746,769 | 5/1998 | Ton et al. . |
| 5,749,883 | 5/1998 | Halpern . |
| 5,749,891 | 5/1998 | Ken et al. . |
| 5,749,894 | 5/1998 | Engelson . |
| 5,749,918 | 5/1998 | Hogendijk et al. . |
| 5,749,921 | 5/1998 | Lenker et al. . |
| 5,766,161 | 7/1998 | Globerman . |
| 5,788,653 | 8/1998 | Lorenzo . |
| 5,797,957 | 8/1998 | Palmer et al. . |
| 5,800,455 | 9/1998 | Palermo . |
| 5,800,526 | 9/1998 | Anderson et al. . |
| 5,814,062 | 9/1998 | Sepetka et al. . |
| 5,824,059 | 10/1998 | Wijay . |
| 5,944,733 * | 8/1999 | Engelson ............................ 606/191 |
| 5,947,963 | 9/1999 | Guglielmi . |
| 5,984,929 | 11/1999 | Bashiri et al. . |
| 5,989,242 * | 11/1999 | Saadat et al. ............................ 606/1 |
| 6,059,815 * | 5/2000 | Lee et al. ............................ 606/209 |

FOREIGN PATENT DOCUMENTS

| | | |
|---|---|---|
| 0 278 937 | 8/1988 | (EP) . |
| 0 382014 A1 | 8/1990 | (EP) . |
| 0 518 704 A1 | 12/1992 | (EP) . |
| 0 627 201 A1 | 12/1994 | (EP) . |
| 592182 | 7/1925 | (FR) . |
| 2 066 839 | 7/1981 | (GB) . |
| WO 92/14408 | 3/1992 | (WO) . |
| WO 94/16629 | 8/1994 | (WO) . |
| WO 95/18585 | 7/1995 | (WO) . |
| WO 95/21592 | 8/1995 | (WO) . |
| WO 97/48351 | 12/1997 | (WO) . |

OTHER PUBLICATIONS

Christos A. Athanasoulis, M.D., The New England Journal of Medicine, May 15, 1980, "Therapeutic Applications of Angiography" pp. 1117–1125 (1 of 2).

Christos A. Athanasoulis, M.D., The New England Journal of Medicine, May 22, 1980, "Therapeutic Applications of Angiography" pp. 1174–1179 (2 of 2).

Alex Berenstein, M.D. and Irvin I. Kricheff, M.D., "Catheter and Material Selection for Transarterial Embolization: Technical Considerations" Radiology, Sep 1979; pp. 631–639.

O.A. Battista, et al. Journal of Applied Polymer Science 1967 "ColloidalMacromolecularPhenomena. Part II. Novel Microcrystals of Polymers" pp. 481–498.

Sadek K. Hilal, M.D. et al. Journal of Neurological Surgery "Therapeutic Percutaneous Embolization of Extra–Axial Vascular Lesions of the Head, Neck and Spine" Sep., 1975; pp. 275–287.

Stephen L. Kaufman, M.D. et al. Investigative Radiology, May–Jun. 1978, "Transcatheter Embolization with Microfibrillar Collagen In Swine"; pp. 200–204.

Ashok J. Kumar, et al., Journal of Neuroradiology (1982) "Preoperative Embolization of Hypervascular Head and Neck Neoplasms Using Microfibrillar Collagen", pp. 163–168.

Richard E. Latchaw, M.D. et al., Radiology (1979) "Polyvinyl Foam Embolization of Vascular and Neoplastic Lesions of the Head, Neck and Spine" pp. 669–679.

Stewart R. Reuter, M.D. et al. American Journal of Radiology, Sep. 1975, "Selective Arterial Embolization for Control of Massive Upper Gastrointestinal Bleeding" pp. 119–126.

Glenn H. Roberson, et al., American Journal of Radiology, Oct. 1979, "Therapeutic Embolization of Juvenile Angiofibroma" pp. 657–663.

Sidney Wallace, M.D. et al., Cancer, Oct. 1979, "Arterial Occlusion of Pelvic Bone Tumors"; pp. 322–325 & 661–663.

"Mechanical Devices for Arterial Occlusion" By C. Gianturco, M.D., et al., July 1975, pp. 428–435.

"Therapeutic Vascular Occlusion Utilizing Steel Coil Technique: Clinical Applications" By Sidney Wallace, et al., Am J. Roentgenol (1976); pp. 381–387.

"Transcatheter Intravascular Coil Occlusion of Experimental Arteriovenous Fistulas", By James H. Anderson, et al., Am. J. Roentgenol, Nov. 1977, pp. 795–798.

"Mini Gianturco Stainless Steel Coils for Transcatheter Vascular Occlusion" By James H. Anderson, et al., from the Department of Diagnostic Radiology at the University of Texas System Cancer, Aug. 1978, pp. 301–303.

"A New Improved Coil for Tapered–Tip Catheter for Arterial Occlusion" By Vincent P. Chuang, M.D., et al., May 1980, pp. 507–509.

* cited by examiner

ENDOLUMINAL DEVICE DELIVERY SYSTEM USING AXIALLY RECOVERING SHAPE MEMORY MATERIAL

BACKGROUND OF THE INVENTION

1. Field of the Invention

This invention relates generally to therapeutic placement of interventional medical devices into the vasculature of the human body. More particularly, this invention concerns a placement system using heat-activated shape memory materials to release endoluminal devices at a desired location within the body.

2. Description of Related Art

A type of interventional medical device known as an endoluminal coil is used for a wide variety of therapeutic purposes including the treatment of intracranial vascular aneurysms. A vascular aneurysm is often formed as the result of an abnormal dilation of a blood vessel which weakens the arterial wall and allows it to expand into an adjacent body tissue or cavity. Intracranial aneurysms may be treated to prevent rupturing by placing endoluminal coils through the neck of an opening from the vessel into the interior cavity of the aneurysm. After placement, the coils pose a physical barrier, reducing blood flow into the aneurysm and promoting the formation of an embolus in the aneurysm cavity. The embolus formation in the aneurysm cavity further impedes blood flow into the aneurysm and reduces the blood pressure against the aneurysm wall, thus reducing the possibility of a rupture.

One known method for delivering coils into an intracranial aneurysm involves the use of a catheter and a guidewire with a detachable tip shaped in the form of a coil. Such a system is described in U.S. Pat. No. 5,312,415 which is incorporated herein by reference. Microcatheters are known, for example, that allow for navigation into cerebral arteries and entry into intracranial aneurysms. The catheter is guided through the vasculature using a guidewire until it reaches the desired location. The tip of the guidewire is then detached and the coils are pushed into the aneurysm until they occlude at least a portion of the interior of the aneurysm. Although generally effective, this technique has limitations on the accuracy for precision placement of embolic coils in intracranial aneurysms. It would be particularly desirable to have a simple delivery system which allows for precise positioning of embolic coils and virtually instantaneous release once the coils are in place.

One approach which provides for greater accuracy of placement involves attaching a coil to the end of a guidewire and maneuvering the guidewire to place the embolic coil in the desired location and then releasing the coil from the guidewire. Since the physician has control of the guidewire and the coil is firmly attached to the distal end of the pusher, it is possible to achieve a much higher degree of placement accuracy with this approach. However, to implement this approach, the delivery system must include a release mechanism which can be used to easily decouple the coil from the guidewire while inside tiny blood vessels. A variety of release mechanisms have been proposed for this purpose.

In one known technique for deploying an endoluminal device, endoluminal coils may be released through electrolytic dissolution of a connecting segment between the coil and the distal tip of the guidewire. This method typically involves the application of a positive direct current for a predetermined amount of time which results in the dissolution of a stainless steel connector which holds the coil to the guidewire. Although this method has met with considerable success, the procedure has significant disadvantages. Because the use of electrolytic dissolution is slow and unreliable, the delivery of the devices can be very time consuming and therefore very costly. The increased surgery time also creates a higher risk for the patient. In addition, the secondary effects of dissolving a stainless steel wire in the blood could possibly be detrimental to the patient. For these reasons, a simpler, faster, safer and more reliable method of delivering the devices is needed.

Detachable coil assemblies are also known that use a threaded coupling such that the coil is released when the guidewire is rotated. Another conventional technique uses a heat-releaseable adhesive bond to separate the coils from the distal end of the catheter. When laser energy is transferred via a fiber optic cable to the connector, the connector is heated, thereby releasing the heat-sensitive adhesive bond between the connector and coil.

One known implant delivery assembly is activated thermally, and includes a coupling portion made of a shape memory material that interlockingly engages the implant when the shape memory material is in one configuration, and releases the implant in another configuration. The implant is detachably coupled to a pusher formed of shape memory material that allows thermal activation of the decoupling mechanism. The coupling portion is constructed with a deformed shape for holding the implant to the pusher, and a pre-set shape that provides release of the implant when the thermal activation is provided. The coupling portion of the pusher is heated by passing an electric current between the pusher and the body of the patient.

Another detachable embolic coil assembly is known that uses interlocking clasps that are used in a surgical instrument for delivering an embolic coil to a selected site within the vasculature of the human body.

Yet another known embolic coil assembly includes a ball that is forced through an aperture in a socket on the distal end of a pusher to release the coil. After a catheter is inserted and navigated through the vessel, and the coil is in place, a plunger is advanced to press the ball and its coil into the target site.

Some conventional vasoocclusive devices are operated by pulling or jerking the catheter tip from an inflatable balloon, thus potentially compromising the position of the implant. One such device provides for an endovascular wire and tip that can be separated from the holding wire mechanically or electrolytically for the formation of thrombus in blood vessels. However, such devices that release the interventional device by mechanically breaking an intermediate section between the catheter tip and balloon can potentially leave broken or jagged ends that could injure the vasculature.

One conventional releaseable balloon catheter used to embolize vascular lesions has a tubular portion made of a material such as a hydrophilic polymer located between the catheter and the balloon that can be broken by torsion of the tubular portion. The tubular portion can be melted by heating the tubular portion, or can be dissolved in the blood when heated, and electrodes are provided for heating the tubular portion. Another conventional technique for separating a balloon from a balloon catheter involves the melting and breaking of a connecting member made from polyvinyl alcohol or trans-polyisoprene between the balloon and the catheter body when power is supplied to electrodes provided for heating the connecting member. When the connecting member is heated to temperatures of about 70° C. and slight tension is applied, the balloon can be separated from the main catheter body. However, such devices that release the interventional device by melting or dissolving the intermediate section between the catheter tip and balloon can also potentially release undesirable particles from the connecting member into the bloodstream.

From the above, it can be seen that a variety of approaches to placing embolic devices have been developed, but all of them are limited in some way by the time to release, the dispersion of particles or chemicals, the introduction of electricity, mechanical force on the implant after placement, or some combination of these affects. There is therefore a need for a precise, controlled method of deploying therapeutic interventional devices without compromising the position of the implant, without presenting broken or jagged ends that can potentially injure the vasculature, and without release undesirable particles or materials into the bloodstream.

Recently, a release system for vasoocclusive coils has been developed involving the use of a microgripper made of shape memory material. The shape memory microgrippers is mechanically actuated by the conversion of laser light to heat energy. Another newly developed type of release mechanism using shape memory materials involves a tube of radially recovering shape memory polymer attached to the distal end of an optical fiber pusher. A device such as an endoluminal coil is introduced into the tube and the tube is compressed or crimped around the end of the coil to hold it in place. Once the coil is in the desired location in the vasculature, the tube of shape memory polymer is heated by passing light through the optical fiber pusher to the distal end of the pusher, thereby causing the tube to recover its original diameter and shape. After the tube has recovered its original shape, it is no longer compressed or crimped around the device and the device is free to slip out of the tube.

In another approach, an endoluminal coil delivery system is provided with a mechanical release mechanism for positioning and delivering a coil within a lumen that utilizes a mechanical latch to engage the coil during positioning. The coil is placed at the distal end of delivery system and includes a fitting at the end of coil which is engaged by jaws. The coil is released from the jaws by advancing a release tube over the jaws, which squeezes the jaws, thereby disengaging them from the fitting.

A shape memory metal actuated separation device is also known that can be used for spacecraft. A segmented nut engages a threaded bolt that is to be held and released and is held together by a nut retainer that is movable with respect to the nut and affixed to a shape memory alloy element. The shape memory alloy element is heated by an electrical resistance heater, thereby moving the retainer which causes disengagement.

In one coil shaped intravascular stent formed into a coil spring, to be used to reinforce an arterial wall, the wire forming the stent has axially spaced rollers or bearings to facilitate advancement and withdrawal of the coil spring, with enlarged beads between the rollers to hold the rollers away from one another.

While the use of shape memory polymers for release of vasoocclusive coils has shown great promise, the use of radially recovering shape memory polymers has not been completely satisfactory; the primary problem recently encountered with radially recovering tubes being that shape memory polymers tend to remold themselves around devices which exert external forces upon them, the tube of shape memory polymer then tending to remold itself around the endoluminal coil thereby causing problems during the attempted release. In a situation in which the device does not completely detach from the pusher, the coil may be inadvertently pulled part or all of the way back out of the vasculature malformation and into the parent vessel or the vasculature. Since proper positioning of the intravascular device is critical to the successful treatment of intracranial aneurysms, a reliable method of delivering and placing the devices is critically important. The present invention meets these and other needs.

SUMMARY OF THE INVENTION

Briefly, and in general terms, the present invention provides an endoluminal device delivery system which uses a shape memory material to release endoluminal devices to permit the controlled delivery of such endoluminal devices into a human body. In one presently preferred embodiment, the invention comprises an optical fiber pusher used to navigate through the body lumens and a short tubular collar of shape memory material which surrounds the distal end of the pusher, similar to a sheath, to deliver the therapeutic device at the site in the vasculature to be treated, and that axially recovers to release the therapeutic device at the desired site. Alternatively, the tubular collar can be formed to recover axially and radially to release the therapeutic device at the desired site.

In one presently preferred aspect of the invention, the proximal end of the tubular collar can be attached to the distal end of the pusher. When the tubular collar is relaxed, the distal end of the pusher extends slightly beyond the distal end of the tubular collar. However, by heating the tubular collar above its glass transition temperature ($T_g$), the tubular collar of shape memory material transitions into the rubbery state and is axially stressed in the distal direction to increase its length. In the elongated state, the distal end of the tubular collar extends beyond the distal end of the pusher creating a tubular collar at the end of the delivery device. Because the tubular collar is formed from a shape memory material, it will return to its original in the absence of external stress. However, before the tubular collar can recover its original shape, it is fixed in the elongated position by lowering the temperature of the material below $T_g$ thereby transitioning the shape memory material back to the glassy state. The tubular collar, which extends beyond the end of the pusher, is then used as a means for holding endoluminal devices. The collar can also be radially compressed around an end portion of a therapeutic device to mechanically engage the therapeutic device. An proximal end portion of the therapeutic device can be also engaged through an adhesive bond with the collar or other similar means.

In another presently preferred embodiment, a shape memory material assisted interlocking delivery system is provided with an interlocking assembly at the stem portion of the endoluminal therapeutic device to releaseably connect the endoluminal therapeutic device to the elongated pusher member. The interlocking assembly includes first and second interlocking members having surfaces defining corresponding interlocking mating shapes. One of the interlocking members is mounted to the distal portion of the elongated pusher member, and the second interlocking member is mounted to the stem portion of the endoluminal therapeutic device. The body of shape memory material has an axially stressed configuration engaging the interlocking assembly and an axially recovered configuration withdrawn from the interlocking assembly to release the endoluminal therapeutic device from said body of shape memory material. The present invention provides important benefits to such an interlocking configuration compared to prior art devices. By retracting both axially and radially, reliable detachment of the interlocking elements is facilitated, since no part of the SMP collar surrounds the interlocking elements after activation.

After the device is inserted into the vasculature and is maneuvered into the desired location, heat is transferred to the tubular collar of shape memory material from the pusher through passage of light energy, heat pipe, electrical resistance, radio-frequency electromagnetic waves, ultrasonic waves or other means. The heat transfer causes the temperature of the tubular collar to once again rise above $T_g$ and the tubular collar transitions back into the rubbery state, radially expands, and axially retracts to its original shape. As the tubular collar recovers its original shape, it retracts back over the stem end portion of the therapeutic device engaged by the collar. As the collar retracts, the therapeutic device engaged by the tubular collar engages a stop at the end of the pusher. Preferably, the stop at the end of the pusher is specifically formed to engage the therapeutic device. As the tubular collar continues to recover axially, the stop prevents the therapeutic device from moving proximally with the tubular collar and the therapeutic device is thereby dislodged from the tubular collar. After the tubular collar has completely recovered its original shape, the tubular collar no longer encapsulates the stem end portion of the therapeutic device, and therefore the therapeutic device is decoupled from the delivery system.

This method produces a simple, predictable and reliable means for the release of endoluminal devices into the body. Using this method, the placement of endoluminal devices can be accomplished in a minimally invasive manner in a short period of time with more reliability and less risk to the patient than with other methods. This method also allows for precise positioning of the therapeutic devices since the physician has complete control over the therapeutic device's position until the release is triggered by the application of heat to the collar as a result of energy transfer through the pusher.

In another presently preferred embodiment, the stem end portion of the therapeutic device that is mechanically engaged by the tubular collar comprises one or more rounded members that are attached to the stem end portion of the therapeutic device, such as by solder, welding or adhesive, or the like, or otherwise formed in the stem portion of the therapeutic device. Each rounded members can be formed, in one presently preferred aspect of the invention, as one or more substantially rounded balls attached to the stem end portion of the therapeutic device; or alternatively, they may be formed as one or more substantially rounded coils of wire attached to the stem portion of the therapeutic device. The rounded members thus allow the tubular collar to effectively grip the stem portion of the therapeutic device, and provide a blunt stem on the therapeutic device to help prevent injury to the vasculature by the stem of the therapeutic device after the therapeutic device is deployed at the site in the vasculature to be treated. Release is triggered by the application of heat to the collar as a result of energy transfer through the pusher.

In a preferred alternate embodiment, the tubular collar can be bonded to the stem portion of the therapeutic device, such as by solder, welding or adhesive, or the like, and a modified distal end of the pusher, modified to have additional ridges, for example, is mechanically engaged by the tubular collar. Release is triggered by the application of heat to the collar as a result of energy transfer through the pusher.

In another preferred alternate embodiment, the stem portion of the therapeutic device comprises one or more rounded members are attached to the stem portion of the therapeutic device, such as by solder, welding or adhesive, or the like, or otherwise formed in the stem portion of the therapeutic device, and the tubular collar is bonded to the rounded members of the stem portion of the therapeutic device, such as by solder, welding or adhesive, or the like. The distal end of the pusher is mechanically engaged by the tubular collar, and release is triggered by the application of heat to the collar as a result of energy transfer through the pusher.

In another alternate preferred embodiment, the body of shape memory material is bonded to the distal end of the elongated pusher member and to the stem portion of the endoluminal therapeutic device, and the body of shape memory material is scored along a line of scoring between the elongated pusher member and the stem portion of the endoluminal therapeutic device to break along the line of scoring when the body of shape memory material changes from the stressed configuration to the recovered configuration to dislodge the endoluminal therapeutic device from the elongated pusher member. The body of shape memory material is preferably a tubular collar, and can have a middle portion of narrowed thickness at the line of scoring, or a middle portion of narrowed diameter.

In another alternate preferred embodiment, the invention comprises an endoluminal device delivery system with an elongated pusher member having a distal end, a body of shape memory material mounted to the distal end of the elongated pusher member, and a collet mounted to the pusher member and disposed within the body of shape memory material for releaseably retaining the therapeutic device. The body of shape memory material can be a shape memory polymer, such as polyurethane, or a nickel titanium alloy, for example. The body of shape memory material has a stressed configuration engaging the collet, that in turn engages a stem portion of the endoluminal therapeutic device, and a recovered configuration withdrawn from the stem portion of the endoluminal therapeutic device. The proximal end of the collet is mounted to the distal end of the pusher member, and the distal end of the collet has a plurality of gripping arms movable between closed and open configurations, for mechanically releaseably retaining the stem portion of the endoluminal therapeutic device. The collet can, for example, be formed of a material such as nickel titanium alloy or spring steel, and the proximal end of the collet can be tubular, for receiving the distal end of the pusher member. The distal gripping arms are also preferably configured to provide a sufficient space for receiving and for mechanically releaseably retaining the proximal portion of an endoluminal therapeutic device. The proximal end portion of the therapeutic device that is mechanically engaged by the collet comprise one or more rounded members that are attached to the stem end portion of the therapeutic device. The body of shape memory material preferably comprises tubular collar, that can be axially stressed, or axially and radially stressed, to engage said collet to releaseably retain the stem portion of the endoluminal therapeutic device, which can, for example, be an embolic coil.

Those skilled in the art will also recognize that, while the invention has been described in the context of an endoluminal device delivery system, other similar device delivery systems may also benefit from the invention. The advantages of the invention will become apparent from the following detailed description and the accompanying drawings, which illustrate by way of example the features of the invention.

DETAILED DESCRIPTION OF THE PREFERRED EMBODIMENTS

Figure 1:
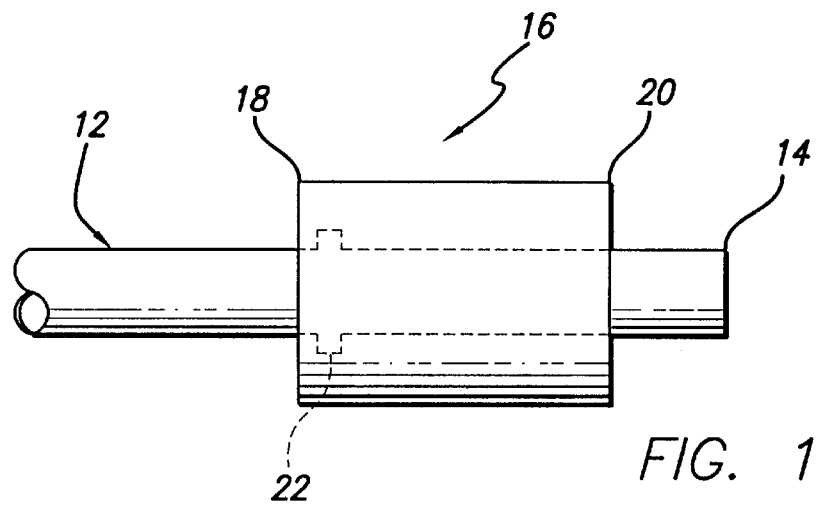
FIG. 1 is a side view of a pusher with a tubular collar of shape memory material located at its distal end in a stress relieved state.
Figure 1A:
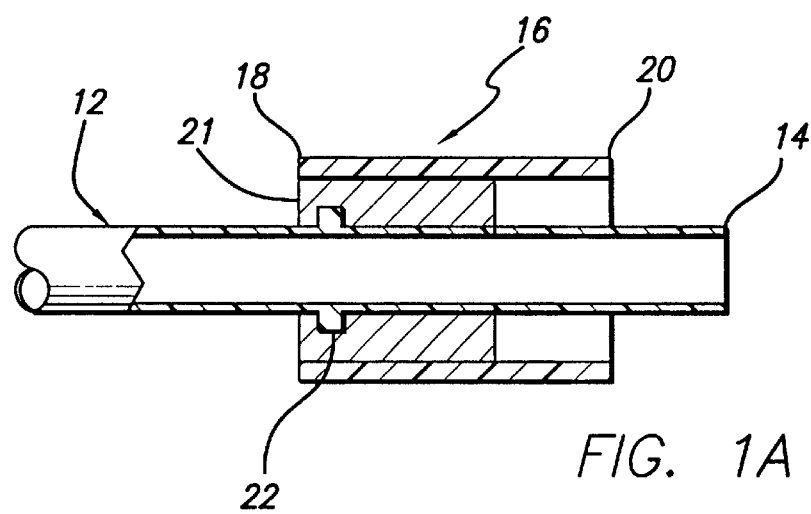
FIG. 1A is a cross-sectional view of the apparatus of FIG. 1.

As very small medical instruments such as microcatheters have become available, physicians are now able to reach areas within the human body which were previously inaccessible. Among the areas which can now be accessed in a minimally invasive procedure are the tiny blood vessels within the brain. Using very small diameter pushers, it is now possible to insert therapeutic devices through microcatheters to treat damaged vasculature within the brain such as intracranial aneurysms. However, because the pushers and catheters used to deliver these devices are so small, there are practical limitations associated with their use. For example, because of the size and delicacy of the devices, it is not practical to have a device with complex moving parts at the distal end of the pusher, even though it is important to be able to reliably release the device from the pusher into the vasculature. Various methods have been developed to overcome this problem in the prior art.

For example, one prior art method for releasing tiny medical devices into the body is to solder the device to the end of a stainless steel guidewire and then release the device by applying an electrical current to the guidewire which dissolves a portion of the stainless steel wire. Another known method utilizes a heat-sensitive adhesive which is used to bond the device to the end of a fiber optic cable. The device is released by shining laser light through the optical fiber, which heats the adhesive and releases the bond. Although these and other methods have shown some promise, none has shown to be a definitive solution to the need for rapid and reliable release of vasoocclusive devices into tiny areas of the vasculature.

As shown in the drawings, which are included for purposes of illustration and not by way of limitation, in one presently preferred embodiment, the endoluminal device delivery system comprises an optical fiber used as an elongated pusher 12 having a proximal end and a distal end 14, the distal end of the optical fiber being sheathed in a tubular collar of shape memory polymer 16 with a proximal end 18 and a distal end 20. The optical fiber can be sized to be quite flexible and bend sufficiently to follow the body lumen. Alternatively, the elongated pusher can be formed of suitable materials for conducting radio frequency energy, magnetic energy, or ultrasonic energy, such as an elongated metal member, for example, or of a heat pipe for conducting heat from a heat source, to cause the tubular collar to axially recover its original shape. The proximal end of the tubular collar 18 may be retained on the pusher by radial protrusions 22 near the distal end of the pusher, or, alternatively, retained by an adhesive bonding material. In the unstressed state, the tubular collar will typically have an essentially constant inner and outer diameter extending from its proximal end to its distal end. In practice, after the tubular collar has been placed over the end of the pusher, the collar 20 is adhesively attached to pusher 12 by an adhesive which has a higher melting point than the transition temperature of the shape memory material. In one preferred embodiment, an adhesive found to be useful for such purposes is cyanoacrylate adhesive, such as is available from Loctite Corporation of Connecticut, or under the trade name "APOLLO" from Cyberbond of Illinois.

Figure 2:
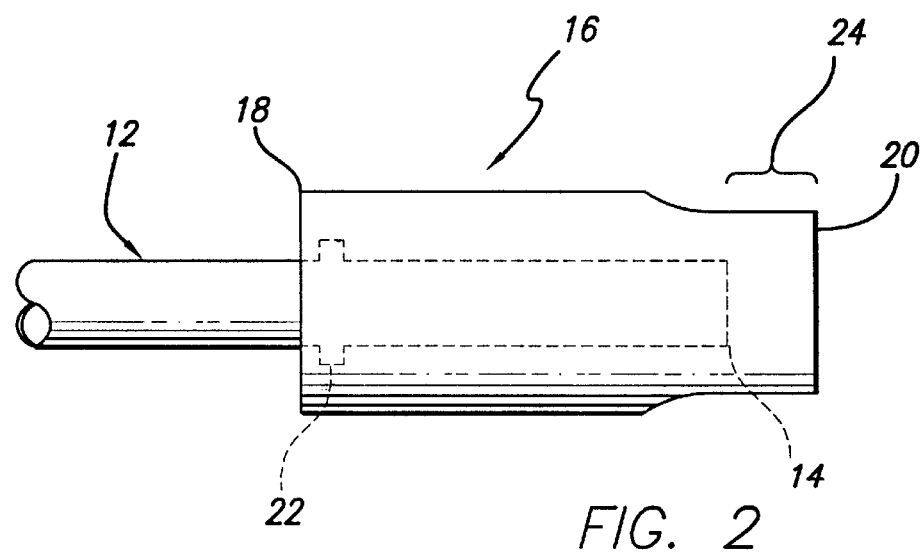
FIG. 2 is a side view of the pusher with the shape memory material after it has been axially stressed and quenched in the elongated position.

FIG. 2 illustrates the device after the tubular collar of shape memory material has been heated and stressed axially to increase its length so the distal end of the tubular collar extends beyond the distal end of the pusher, providing a length 24 for releaseably securing a stem portion of the endoluminal therapeutic device. The tubular collar can be fixed in the elongated position by quenching the tubular collar to a temperature below $T_g$ which preserves the stressed configuration of the tubular collar. The tubular collar can thus be formed such that an embolic coil may be introduced into the collar and held mechanically within the collar beyond the distal end of the pusher.

Figure 3:
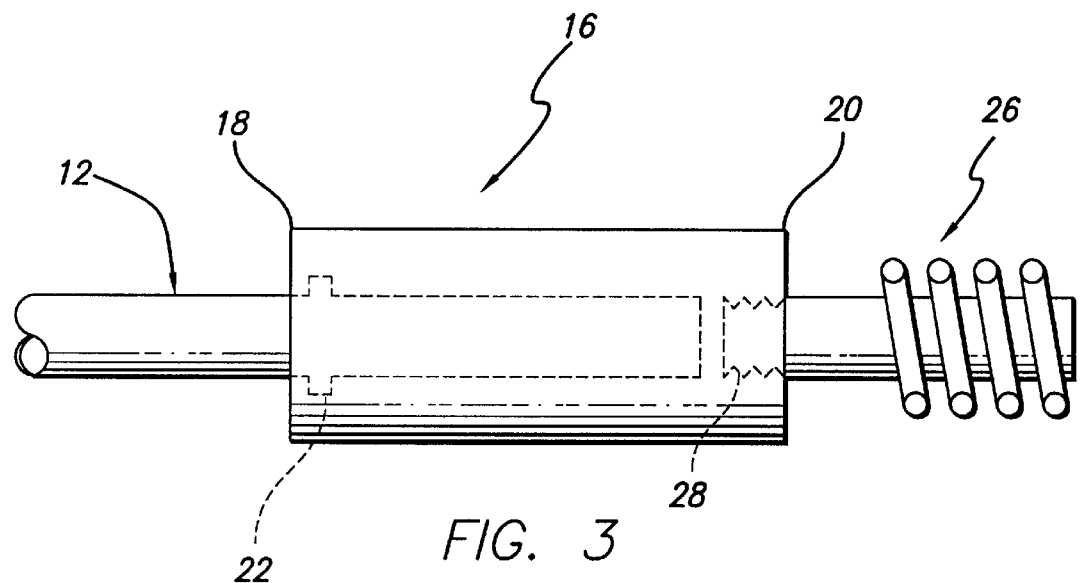
FIG. 3 shows the shape memory material compressed over the medical device.

FIG. 3 illustrates the delivery system of the invention with an embolic coil 26 introduced into the collar. The embolic coil may be mechanically engaged to the collar 24 by compressing or crimping the collar over the coil. The embolic coil may also be formed such that it includes a ribbed extension 28 at its stem end which is specifically designed to fit into the tubular collar and be retained therein when the collar is deformed to engage the extension 28.

Figure 4:
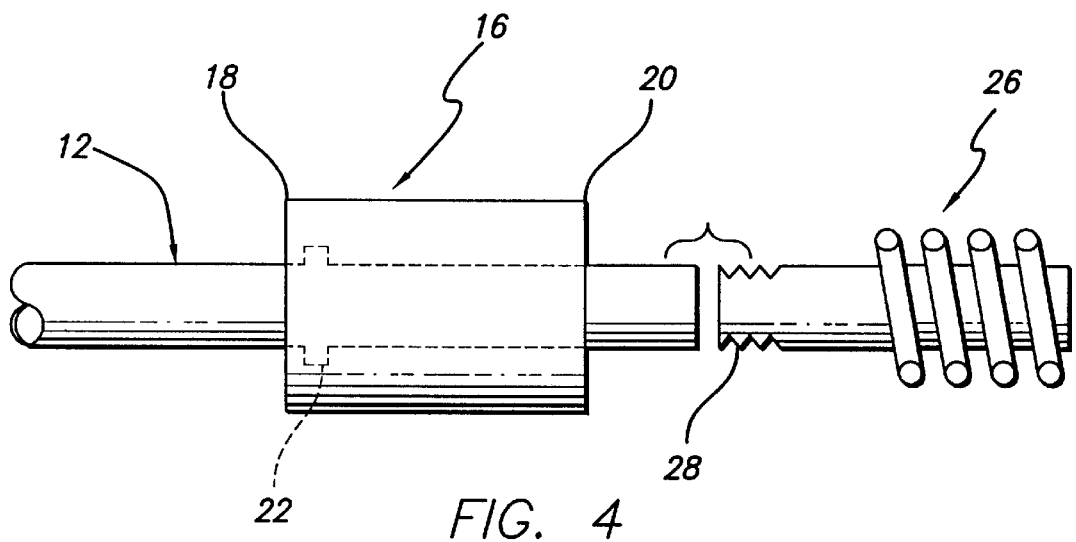
FIG. 4 is a perspective of the shape memory polymer after it has recovered axially to its original length and has released the endoluminal device.

FIG. 4 shows the delivery system after heat has been transferred through the optical fiber to the tubular collar of shape memory polymer, thereby causing it to rise in temperature above $T_g$ and axially recover to its original shape.

In one presently preferred embodiment, the shape memory collar 24 is heated to a temperature which allows it to be shrunk onto coil 26. The collar can additionally attached to elongated pusher 12 by an adhesive which retains high strength at temperatures beyond the shape memory material transition point $T_g$. After insertion, and when the operator is satisfied that the device is properly deployed, light energy from a source of coherent light such as a laser is introduced into the proximal end of the optical fiber (not shown) and propagated to the distal end of the fiber to cause the shape memory material collar to return to its previous shape and release coil. Those skilled in the art will recognize that the invention can also be used with a variety of other placement catheter systems, and it is not intended that the invention be limited to the placement concepts illustrated, which are included by way of example.

The endoluminal therapeutic device delivery system can thus be prepared by attaching a body of shape memory material to the distal end of an elongated pusher member, heating the body of shape memory material to a temperature where shape of the body may be easily altered under stress, stressing the body of shape memory material axially such that the body engages a portion of an endoluminal therapeutic device, and quenching the body to fix its shape. Thereafter, the endoluminal therapeutic device can be delivered into the vasculature of a human body by threading the pusher through a catheter to position the endoluminal therapeutic device, and heating the body of shape memory material such that the body recovers its original dimensions, thereby releasing the endoluminal therapeutic device.

In the alternative preferred embodiments illustrated in FIGS. 5 to 10, the endoluminal therapeutic device delivery system 30 comprises an elongated pusher member 32 having a proximal end and a distal end 34, the distal end of the pusher member being sheathed in a tubular collar 36 of shape memory material having a proximal end 38 and a distal end 40.

The elongated pusher member is, in one presently preferred aspect, formed of an optical fiber which will bend sufficiently to follow the turns and bends of the vasculature when it is introduced, such as through a catheter, into the body. Alternatively, the elongated pusher member can be formed of suitable materials for conducting radio frequency energy, magnetic energy, or ultrasonic energy, such as an elongated metal member, for example, or of a heat pipe for conducting heat from a heat source, to cause the tubular collar to axially recover its original shape. The proximal end 38 of the tubular collar can be attached to the pusher member by a temperature resistant adhesive. In the unstressed state, the tubular collar will typically have a constant inner and outer diameter extending from its proximal end to its distal end.

Figure 5:
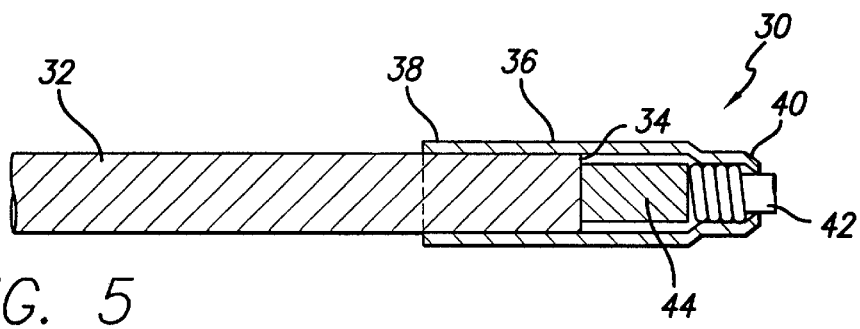
FIG. 5 is a sectional schematic view of another preferred embodiment of an endoluminal therapeutic device delivery system, showing the tubular collar in an axially and radially stressed configuration retaining a stem portion of an endoluminal therapeutic device.

FIG. 5 illustrates the device after the tubular collar 36 of shape memory material has been heated and stressed axially, as well as radially by compressing or crimping the collar over the stem or portion 42 of the endoluminal therapeutic device, to increase its length so the distal end of the tubular sheath extends beyond the distal end of the pusher, and to mechanically releaseably retain the stem 42 of the endoluminal therapeutic device. For simplicity, the distal portion of the endoluminal therapeutic device is not shown. A stop member 44 can advantageously be mounted to the distal end of the pusher member to form the distal portion of the pusher member for dislodging the stem portion of the endoluminal therapeutic device when it has been delivered to the site in the vasculature to be treated. Such a stop member may also be usefully constructed to absorb laser light from the distal end of the optical fiber pusher and convert the light energy to heat energy for heating the collar above the transition temperature $T_g$ of the shape memory material. The tubular collar thus can be formed such that an embolic coil or other endoluminal therapeutic device may be introduced into the collar and held either mechanically, by an adhesive, or other means.

Figure 6:
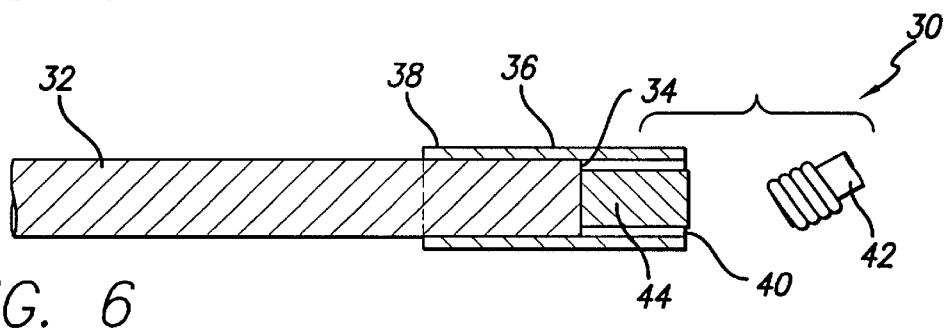
FIG. 6 is a sectional schematic view of the endoluminal therapeutic device delivery system shown in FIG. 5, showing the tubular collar in a relaxed configuration releasing the stem portion of the endoluminal therapeutic device.

FIG. 6 illustrates the delivery system after heat has been transferred through the pusher member to the tubular collar of shape memory polymer, thereby causing it to rise in temperature above $T_g$ and axially recover to its original shape, to release the stem on the stem portion of the endoluminal therapeutic device.

Referring to FIGS. 7 to 10, in another presently preferred embodiment, a shape memory material assisted interlocking delivery system is provided that can be used to deliver devices to any site with control. The endoluminal therapeutic device delivery system can include an interlocking assembly 50 provided to releaseably connect the stem portion of the endoluminal therapeutic device to the elongated pusher member. The interlocking assembly includes a first interlocking clasp member 52 mounted to the distal portion of the elongated pusher member, and a second interlocking clasp member 53 mounted to the stem portion of the endoluminal therapeutic device, such as by adhesive, with the first and second interlocking members having corresponding interlocking mating shapes. The first interlocking member 52 mounted to the distal portion of the elongated pusher member can additionally be mounted to the stop member mounted at the distal end of the pusher member, such as by adhesive. The tubular collar of shape memory material has an axially stressed configuration, illustrated in FIG. 7, engaging the interlocking assembly, and an axially recovered configuration, illustrated in FIG. 8, withdrawn from the interlocking assembly to release the endoluminal therapeutic device from the body of shape memory material.

Figure 8:
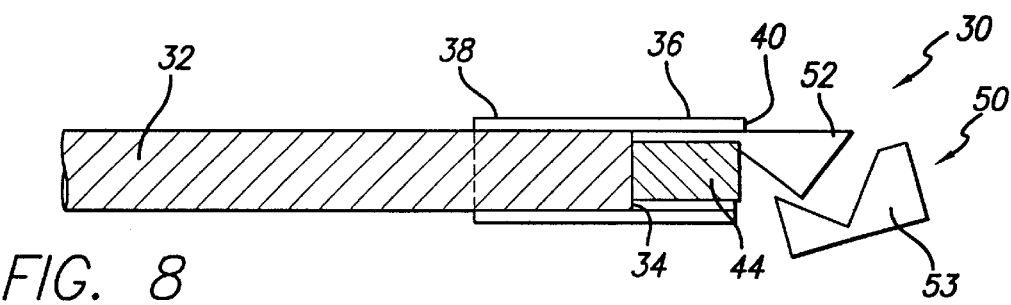
FIG. 8 is a sectional schematic view of the endoluminal therapeutic device delivery system shown in FIG. 7, showing the tubular collar in a relaxed configuration releasing the interlocking assembly.
Figure 9:
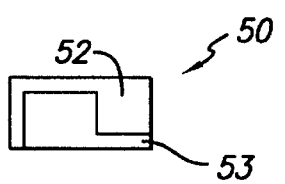
FIG. 9 is a side elevational, schematic diagram of an alternative embodiment of the interlocking assembly.

As is illustrated in FIG. 8, after delivery of the endoluminal therapeutic device to the site in the vasculature to treated has been completed, deployment occurs when the shape memory material is heated to relax the tubular collar to return to an elongated shape, causing the interlocking clasps to fall apart. This delivery only requires the shape memory material to be axially stressed. The shrinking of the polymer occurs over a short length of the tubular collar that can additionally be coated for enhanced lubricity to improve the release of the endoluminal therapeutic device.

Figure 7:
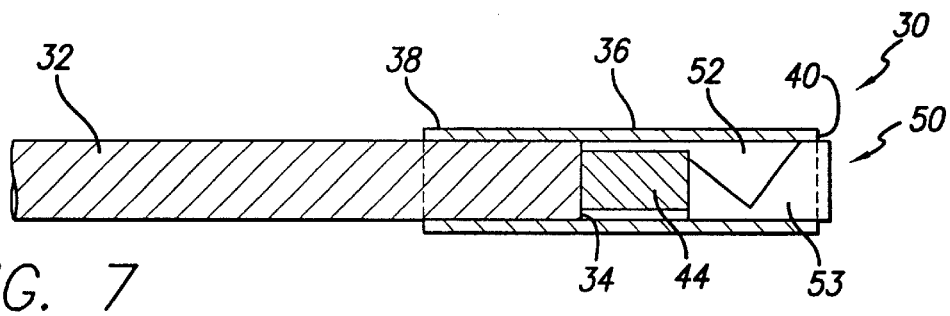
FIG. 7 is a sectional schematic view of another preferred embodiment of an endoluminal therapeutic device delivery system with an interlocking assembly, showing the tubular collar in an axially stressed configuration retaining the interlocking assembly.
Figure 10:
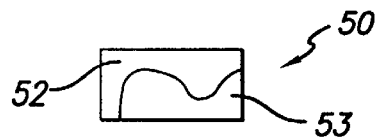
FIG. 10 is a side elevational, schematic diagram of another alternative embodiment of the interlocking assembly.

As is illustrated in FIGS. 7 to 10, the interlocking members of the interlocking assembly can have a wide variety of interlocking, mating shapes, such as the triangular mating surfaces shown in FIG. 7, the rectilinear mating surfaces shown in FIG. 8, or the curved mating surfaces as shown in FIG. 10, for example.

The shape memory tubular collar is preferably heated to a temperature that allows it to be shrunk onto the coil interlocking assembly. The collar can be attached to the elongated pusher by a temperature resistant adhesive, as noted above. After insertion, and when the operator is satisfied that the device is properly deployed, energy can be conducted to the distal end of the pusher member to cause the shape memory material collar to return to its unstressed, relaxed shape, and to release endoluminal therapeutic device. Those skilled in the art will recognize that the invention can also be used with a variety of other placement catheter systems, that the endoluminal therapeutic devices with which the delivery system of the invention can be used include vasoocclusive coils, stents, and the like, and it is not intended that the invention be limited to the placement concepts illustrated by way of example.

In the alternative preferred embodiments illustrated in FIGS. 11 to 14, in which like reference numerals refer to like elements of the foregoing embodiments, the endoluminal therapeutic device delivery system 30' comprises an elongated pusher member 32' having a proximal end and a distal end 34', the distal end of the pusher member being sheathed in a tubular collar 36' of shape memory material having a proximal end 38' and a distal end 40'.

The elongated pusher member is, in one presently preferred aspect, formed of an optical fiber which will bend sufficiently to follow the turns and bends of the vasculature when it is introduced, such as through a catheter, into the body. Alternatively, the elongated pusher member can be formed of suitable materials for conducting radio frequency energy, magnetic energy, or ultrasonic energy, such as an elongated metal member, for example, or of a heat pipe for conducting heat from a heat source, to cause the tubular collar to axially recover its original shape. The proximal end 38' of the tubular collar can be attached to the pusher member by a temperature resistant adhesive. In the unstressed state, the tubular collar will typically have a constant inner and outer diameter extending from its proximal end to its distal end.

Figure 11:
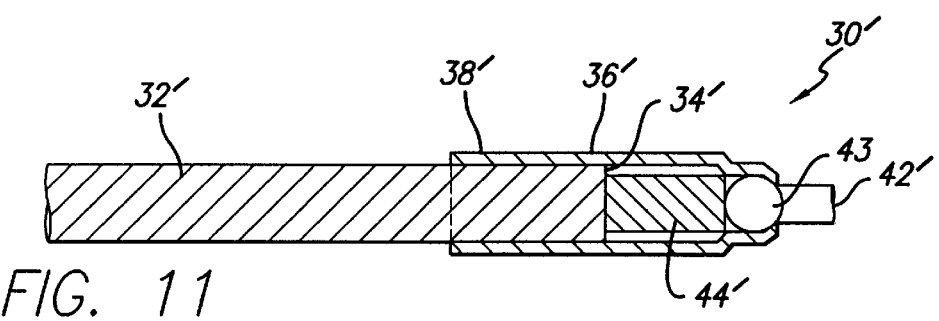
FIG. 11 is a sectional schematic view of another preferred embodiment of an endoluminal therapeutic device delivery system, showing the tubular collar in an axially and radially stressed configuration retaining a rounded member attached to a stem portion of an endoluminal therapeutic device.
Figure 12:
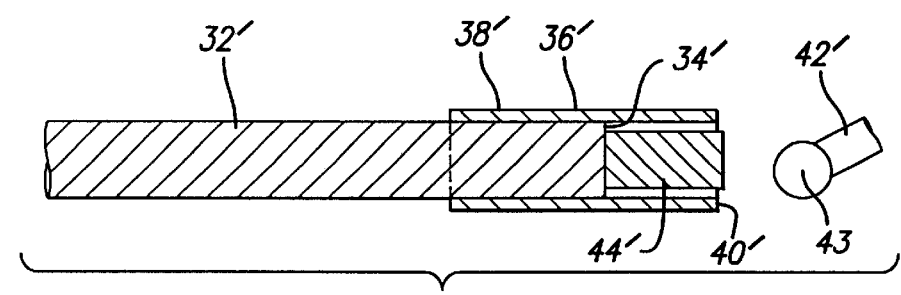
FIG. 12 is a sectional schematic view of the endoluminal therapeutic device delivery system shown in FIG. 11, showing the tubular collar in a relaxed configuration releasing the rounded member of the stem portion of the endoluminal therapeutic device.

FIG. 11 illustrates the device after the tubular collar 36' of shape memory material has been heated and stressed axially, as well as radially by compressing or crimping the collar over the stem or proximal portion 42' of the endoluminal therapeutic device, to increase its length so the distal end of the tubular sheath extends beyond the distal end of the pusher, and to mechanically releaseably retain the stem 42' of the endoluminal therapeutic device. The proximal end portion of the therapeutic device that is mechanically engaged by the tubular collar comprises one or more rounded members 43 that are attached to the stem portion of the therapeutic device, such as by solder, welding or adhesive, or the like, or otherwise formed in the stem portion of the therapeutic device. FIG. 12 illustrates the delivery system after heat has been transferred through the pusher member to the tubular collar of shape memory polymer, thereby causing it to rise in temperature above $T_g$ and axially recover to its original shape, to release the rounded member of the stem on the stem portion of the endoluminal therapeutic device.

Figure 13:
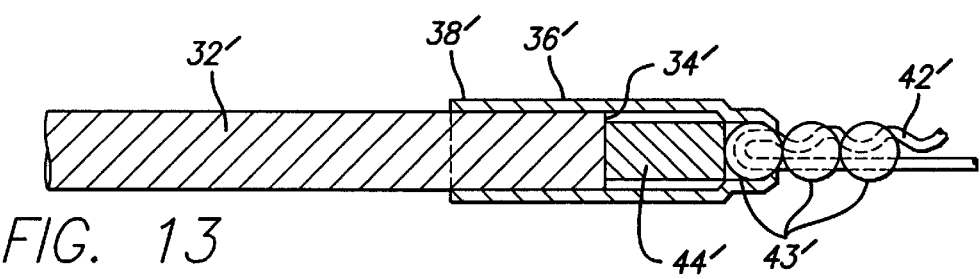
FIG. 13 is a sectional schematic view of another preferred embodiment of an endoluminal therapeutic device delivery system, showing the tubular collar in an axially and radially stressed configuration retaining one of a plurality of rounded members attached to a stem portion of an endoluminal therapeutic device.
Figure 14:
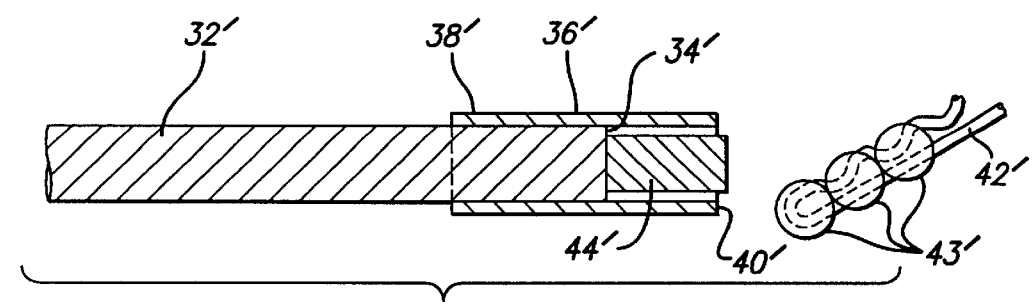
FIG. 14 is a sectional schematic view of the endoluminal therapeutic device delivery system shown in FIG. 13, showing the tubular collar in a relaxed configuration releasing the plurality of rounded members of the stem portion of the endoluminal therapeutic device.

As is illustrated in FIGS. 11 and 12, each rounded members can be formed, in one presently preferred aspect of the invention, as a substantially rounded ball attached to the stem end portion of the therapeutic device; or alternatively, as is illustrated in FIGS. 13 and 14, they may be formed as one ore more substantially rounded coils 43' of wire attached to the stem portion 42' of the therapeutic device, which may be a bent or looped portion of the stem portion of the therapeutic device. The rounded members thus allow the tubular collar to effectively grip the stem of the therapeutic device, and provide a blunt end on the therapeutic device to help prevent injury to the vasculature by the stem portion of the therapeutic device after the therapeutic device is deployed at the site in the vasculature to be treated. FIG. 14 illustrates the delivery system of FIG. 13 after heat has been transferred through the pusher member to the tubular collar of shape memory polymer, thereby causing it to rise in temperature above $T_g$ and axially recover to its original shape, to release the rounded member or members of the stem of the endoluminal therapeutic device.

A stop member 44" can advantageously be mounted to the distal end of the pusher member to form the distal portion of the pusher member for dislodging the stem portion of the endoluminal therapeutic device when it has been delivered to the site in the vasculature to be treated. Such a stop member may also be usefully constructed to absorb laser light from the distal end of the optical fiber pusher and convert the light energy to heat energy for heating the collar above the transition temperature $T_g$ of the shape memory material. The tubular collar thus can be formed such that an embolic coil or other endoluminal therapeutic device may be introduced into the collar and held either mechanically, by an adhesive such as cyanoacrylate, or other means.

Figure 15:
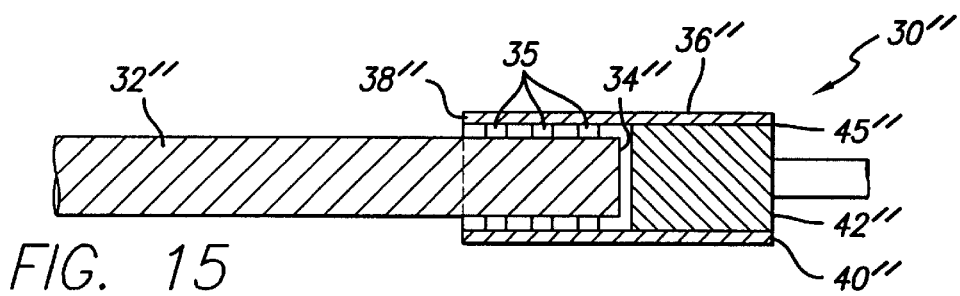
FIG. 15 is a sectional schematic view of another preferred embodiment of an endoluminal therapeutic device delivery system, showing the tubular collar in an axially stressed configuration attached to a stem portion of an endoluminal therapeutic device and gripping a distal modified portion of a fiber optic pusher member.

In the alternative preferred embodiments illustrated in FIGS. 15 to 18, in which like reference numerals refer to like elements of the foregoing embodiments, the endoluminal therapeutic device delivery system 30" comprises an elongated pusher member 32" having a proximal end and a distal end 34", the distal end of the pusher member being sheathed in a tubular collar 36" of shape memory material having a proximal end 38" and a distal end 40". The distal end of the pusher member may have a modified surface, such as by the addition of ridges 35, such as by bonding annular rings to the distal end of the pusher member, such as by cyanoacrylate adhesive, for example. FIG. 15 illustrates the device after the tubular collar 36" of shape memory material has been heated and stressed axially, as well as radially by compressing or crimping the collar over the stem or distal portion 40" of the pusher member, to increase its length so the distal end of the tubular sheath extends onto the distal end of the pusher, and to mechanically releaseably retain the distal end of the pusher member 40". Alternatively, an adhesive bonding material may be used instead of a mechanical lock system of the type described above.

The elongated pusher member is, in one presently preferred aspect, formed of an optical fiber which will bend sufficiently to follow the turns and bends of the vasculature when it is introduced, such as through a catheter, into the body. Alternatively, the elongated pusher member can be formed of suitable materials for conducting radio frequency energy, magnetic energy, or ultrasonic energy, such as an elongated metal member, for example, or of a heat pipe for conducting heat from a heat source, to cause the tubular collar to axially recover its original shape. The distal end 40" of the tubular collar can be attached to the stem 42" of the endoluminal therapeutic device by a temperature resistant adhesive 45", such as cyanoacrylate. In the unstressed state, the tubular collar will typically have a constant inner and outer diameter extending from its proximal end to its distal end.

Figure 16:
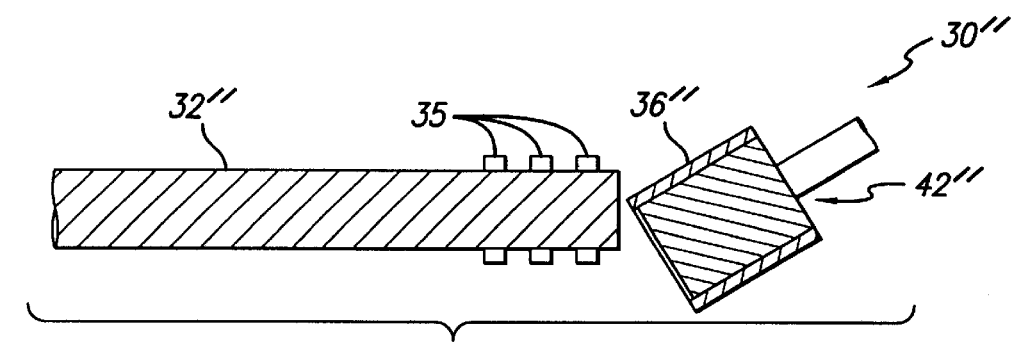
FIG. 16 is a sectional schematic view of the endoluminal therapeutic device delivery system shown in FIG. 15, showing the tubular collar in a relaxed configuration releasing the distal modified portion of a fiber optic pusher member.

FIG. 16 illustrates the delivery system after heat has been transferred through the pusher member to the tubular collar of shape memory polymer, thereby causing it to rise in temperature above $T_g$ and axially recover to its original shape, to release the stem portion of the endoluminal therapeutic device.

Figure 17:
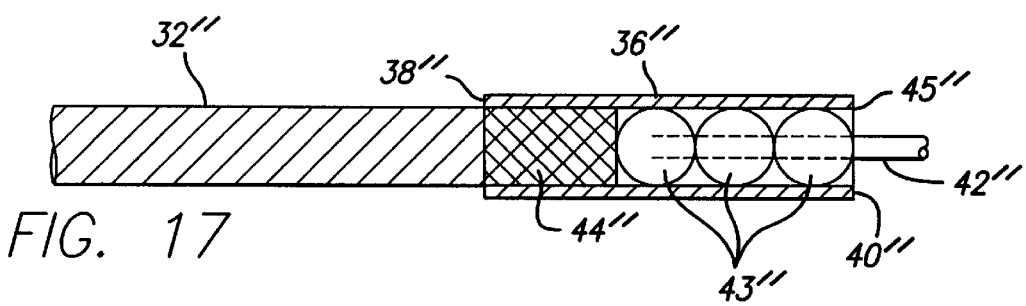
FIG. 17 is a sectional schematic view of another preferred embodiment of an endoluminal therapeutic device delivery system, showing the tubular collar in an axially stressed configuration attached to a plurality of rounded members at a stem portion of an endoluminal therapeutic device and gripping a distal portion of a fiber optic pusher member.
Figure 18:
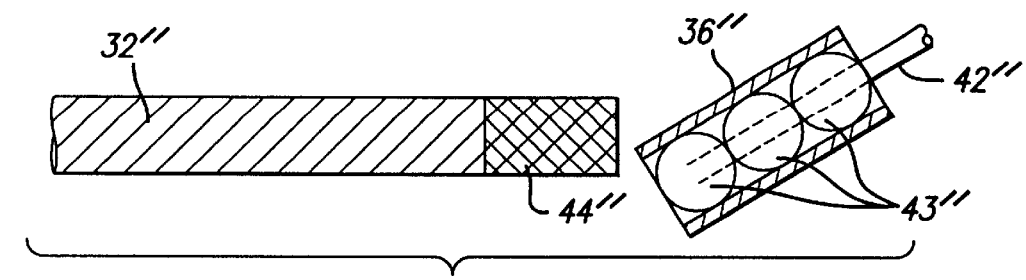
FIG. 18 is a sectional schematic view of the endoluminal therapeutic device delivery system shown in FIG. 17, showing the tubular collar in a relaxed configuration releasing the distal portion of the fiber optic pusher member.

As is illustrated in FIGS. 17 and 18, the stem portion of the therapeutic device that is mechanically engaged by the tubular collar comprises one or more rounded members 43" that are attached to the stem portion of the therapeutic device, such as by solder, welding or adhesive 45", or the like, or otherwise formed in the proximal stem portion of the therapeutic device. Each of the rounded members 43" can be formed, in one presently preferred aspect of the invention, as a substantially rounded ball attached to the stem portion of the therapeutic device; or alternatively, they may be formed as one ore more substantially rounded coils of wire attached to the stem portion 42" of the therapeutic device. A stop member 44''' can advantageously be mounted to the distal end of the pusher member to form the distal portion of the pusher member for dislodging the stem portion of the endoluminal therapeutic device when it has been delivered to the site in the vasculature to be treated. Such a stop member may also be usefully constructed to absorb laser light from the distal end of the optical fiber pusher and convert the light energy to heat energy for heating the collar above the transition temperature $T_g$ of the shape memory material. FIG. 18 illustrates the delivery system of FIG. 17 after heat has been transferred through the pusher member to the tubular collar of shape memory polymer, thereby causing it to rise in temperature above $T_g$ and axially recover to its original shape, to release the distal tip of the pusher member, and to thereby release the stem portion of the endoluminal therapeutic device from the pusher member.

In the alternative preferred embodiments illustrated in FIGS. 19 to 23, in which like reference numerals refer to like elements of the foregoing embodiments, the endoluminal therapeutic device delivery system 30''' comprises an elongated pusher member 32''' having a proximal end and a distal end 34''', the distal end of the pusher member being sheathed in a tubular collar 36''' of shape memory material having a proximal end 38''' and a distal end 40'''. The tubular collar is preferably scored along an annular line of scoring 41, typically around the approximate middle of the tubular collar, to encourage a clean break of the tubular collar along the line of scoring when the tubular is heated to a relaxed state, as will be further explained below.

The elongated pusher member is, in one presently preferred aspect, formed of an optical fiber which will bend sufficiently to follow the turns and bends of the vasculature when it is introduced, such as through a catheter, into the body. Alternatively, the elongated pusher member can be formed of suitable materials for conducting radio frequency energy, magnetic energy, or ultrasonic energy, such as an elongated metal member, for example, or of a heat pipe for conducting heat from a heat source, to cause the tubular collar to axially recover its original shape. The proximal end 38''' of the tubular collar can be attached to the pusher member by a temperature resistant adhesive. In the embodiment illustrated in FIGS. 19 and 20, in the unstressed state, the tubular collar will typically have a constant inner and outer diameter extending from its proximal end to its distal end.

Figure 19:
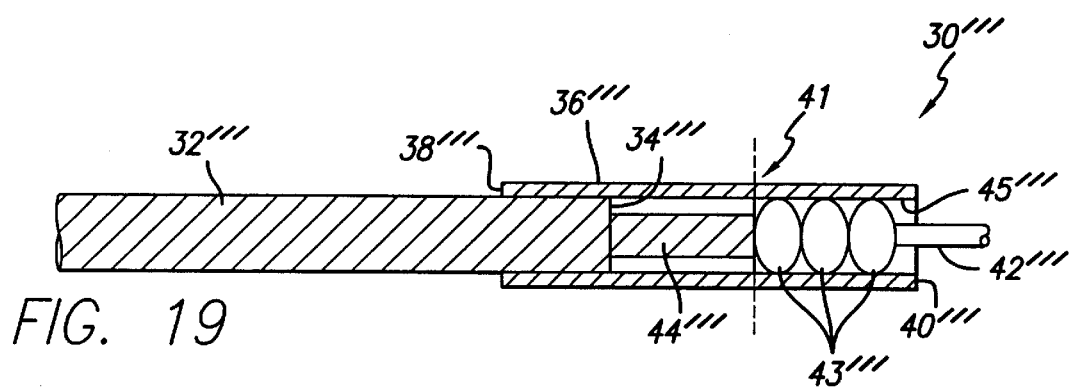
FIG. 19 is a sectional schematic view of another preferred embodiment of an endoluminal therapeutic device delivery system, in which the tubular collar is bonded to both a distal modified portion of a fiber optic pusher member and to a plurality of rounded members at a stem portion of an endoluminal therapeutic device, and is scored to break along the line of scoring, showing the tubular collar in an axially stressed configuration.
Figure 20:
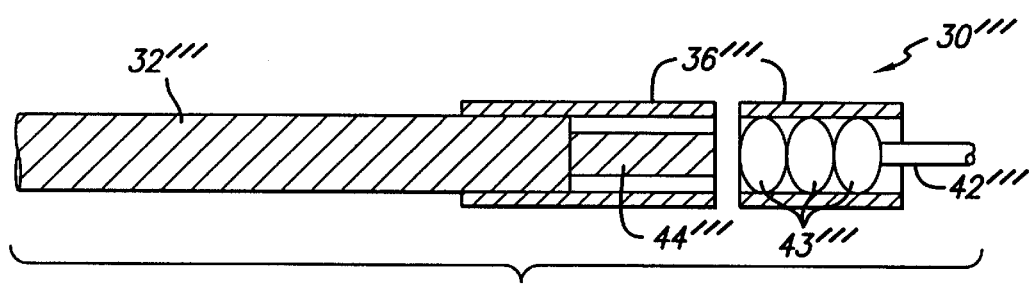
FIG. 20 is a sectional schematic view of the endoluminal therapeutic device delivery system shown in FIG. 19, showing the tubular collar in a relaxed configuration broken along the line of scoring and releasing the endoluminal therapeutic device.

FIG. 19 illustrates the device after the tubular collar 36''' of shape memory material has been heated and stressed axially, and bonded by a layer of adhesive, such as cyanoacrylate, over the stem portion 42''' of the endoluminal therapeutic device, to increase its length so the distal end of the tubular sheath extends beyond the distal end of the pusher, and to mechanically releaseably retain the stem 42''' on the stem portion of the endoluminal therapeutic device. In this embodiment, the stem portion of the therapeutic device to which the tubular collar is bonded comprises one or more rounded members 43''' that are attached to the stem portion of the therapeutic device, such as by solder, welding or adhesive 45''', or the like, or otherwise formed in the stem portion of the therapeutic device. A stop member 44''' can advantageously be mounted to the distal end of the pusher member to form the distal portion of the pusher member for dislodging the stem portion of the endoluminal therapeutic device when it has been delivered to the site in the vasculature to be treated. Such a stop member may also be usefully constructed to absorb laser light from the distal end of the optical fiber pusher and convert the light energy to heat energy for heating the collar above the transition temperature $T_g$ of the shape memory material. FIG. 20 illustrates the delivery system after heat has been transferred through the pusher member to the tubular collar of shape memory polymer, thereby causing it to rise in temperature above $T_g$ and axially recover to its original shape, to break the tubular collar at the line of scoring and release the rounded members of the stem portion of the endoluminal therapeutic device.

Figure 21:
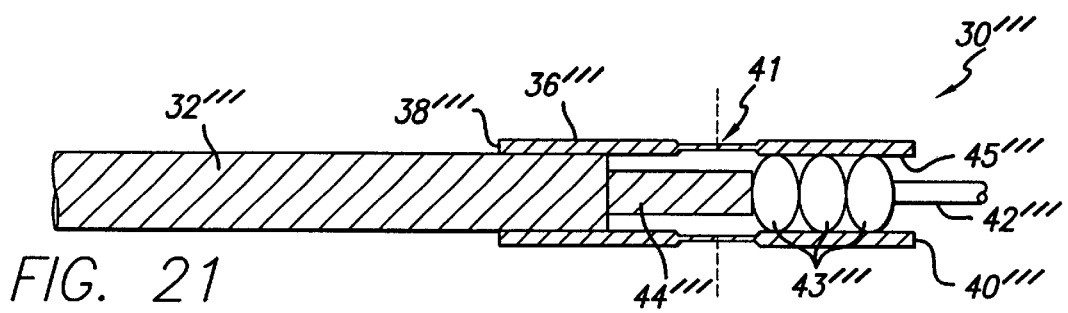
FIG. 21 is a sectional schematic view of another preferred embodiment of an endoluminal therapeutic device delivery system, in which the tubular collar is bonded to both a distal modified portion of a fiber optic pusher member and to a plurality of rounded members at a stem portion of an endoluminal therapeutic device, has a narrowed thickness and is scored to break along the line of scoring, showing the tubular collar in an axially stressed configuration.
Figure 22:
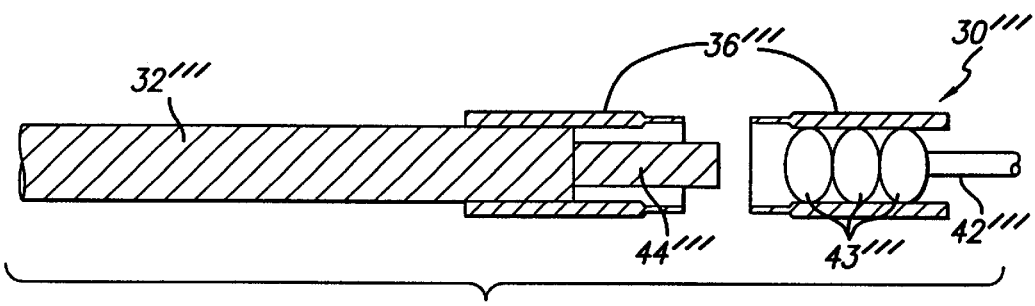
FIG. 22 is a sectional schematic view of the endoluminal therapeutic device delivery system shown in FIG. 21, showing the tubular collar in a relaxed configuration broken along the line of scoring and releasing the endoluminal therapeutic device.

FIG. 21 illustrates a variation of the embodiment of FIGS. 19 and 20, in which the tubular collar is bonded to both a distal portion of a fiber optic pusher member and to a plurality of rounded members at a stem portion of an endoluminal therapeutic device, and has a middle portion 39''' with a narrowed thickness that is scored to break along the line of scoring 41'''. FIG. 22 illustrates the delivery system of FIG. 21 after heat has been transferred through the pusher member to the tubular collar of shape memory polymer, thereby causing it to rise in temperature above $T_g$ and axially recover to its original shape, to break the narrowed thickness portion cleanly along the line of scoring in order to release the rounded members of the stem portion of the endoluminal therapeutic device.

A stop member 44''' is advantageously mounted to the distal end of the pusher member to form the distal portion of the pusher member for bearing against the stem portion of the endoluminal therapeutic device. Such a stop member may also be usefully constructed to absorb laser light from the distal end of the optical fiber pusher and convert the light energy to heat energy for heating the collar above the transition temperature $T_g$ of the shape memory material. The tubular collar thus can be formed such that an embolic coil or other endoluminal therapeutic device may be introduced into the collar and held either mechanically, by an adhesive such as cyanoacrylate, or other means.

Figure 23:
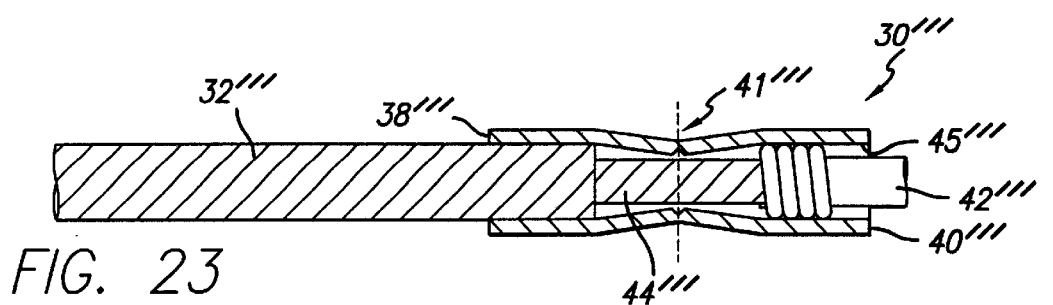
FIG. 23 is a sectional schematic view of another preferred embodiment of an endoluminal therapeutic device delivery system, in which the tubular collar is bonded to both a distal modified portion of a fiber optic pusher member and to a stem portion of an endoluminal therapeutic device, and is necked down and scored to break along the line of scoring, showing the tubular collar in an axially stressed configuration.
Figure 24:
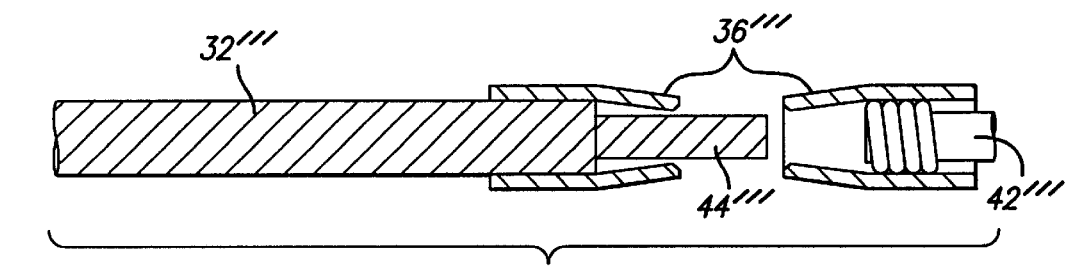
FIG. 24 is a sectional schematic view of the endoluminal therapeutic device delivery system shown in FIG. 23, showing the tubular collar in a relaxed configuration broken along the line of scoring and releasing the endoluminal therapeutic device.

FIG. 23 illustrates another variation of the embodiment of FIGS. 19 and 20, in which the tubular collar is bonded to both a distal portion of a fiber optic pusher member and to a stem portion of an endoluminal therapeutic device, and has a middle portion 39''' that is necked down and scored to break along the line of scoring 41'''. FIG. 24 illustrates the delivery system of FIG. 23 after heat has been transferred through the pusher member to the tubular collar of shape memory polymer, thereby causing it to rise in temperature above $T_g$ and axially recover to its original shape, to break cleanly along the line of scoring in order to release the stem portion of the endoluminal therapeutic device.

A stop member 44''' is advantageously mounted to the distal end of the pusher member to form the distal portion of the pusher member for bearing against the stem portion of the endoluminal therapeutic device. Such a stop member may also be usefully constructed to absorb laser light from the distal end of the optical fiber pusher and convert the light energy to heat energy for heating the collar above the transition temperature $T_g$ of the shape memory material.

In another alternative preferred embodiment illustrated in FIGS. 25 to 28, in which like reference numerals refer to like elements of the foregoing embodiments, the endoluminal therapeutic device delivery system 130 comprises an elongated pusher member 132 having a proximal end and a distal end 134, the distal end of the pusher member being sheathed in a tubular collar 136 of shape memory material having a proximal end 138 and a distal end 140. A stop member 144 can also be mounted to the distal end of the pusher member to form the distal portion of the pusher member.

Figure 25:
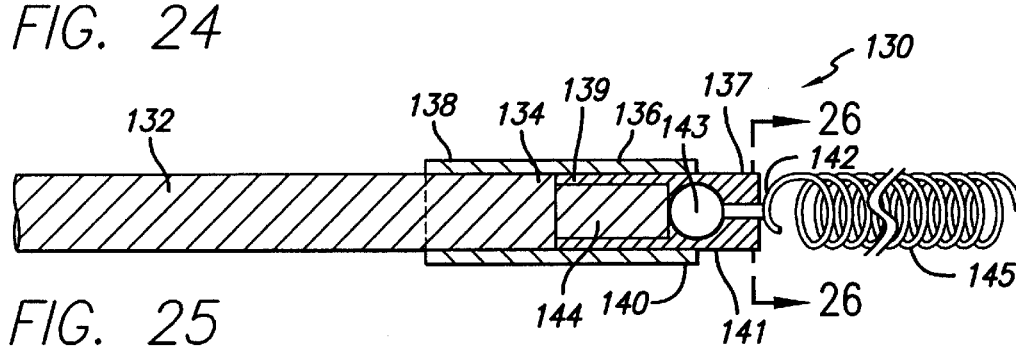
FIG. 25 is a sectional schematic view of another preferred embodiment of an endoluminal therapeutic device delivery system, showing the tubular collar in an axially and radially stressed configuration retaining a rounded member attached to a stem portion of an endoluminal therapeutic device.
Figure 27:
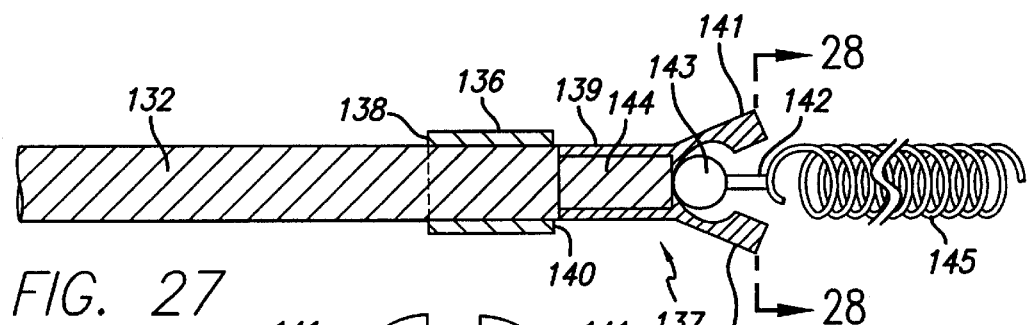
FIG. 27 is a sectional schematic view of the endoluminal therapeutic device delivery system shown in FIG. 25, showing the tubular collar in a relaxed configuration releasing the rounded member of the stem portion of the endoluminal therapeutic device.

Referring to FIGS. 25 and 27, a collet 137 having a proximal tubular end 139 and a distal end with a plurality of gripping arms or prongs 141, is preferably mounted to the distal end of the pusher member, such as by an adhesive such as cyanoacrylate, for example, and within the shape memory tubular collar. The proximal end of the collet is preferably tubular so as to fit over the distal end of the pusher member, and the distal gripping arms or prongs also provide a sufficient space for receiving and for mechanically releaseably retaining the stem portion 142 of an endoluminal therapeutic device 145, such as an embolic coil. The collet is preferably formed of a nickel titanium alloy such as NITINOL, or spring steel, that retains the gripping arms or prongs of the collet in a closed configuration, for mechanically releaseably retaining the stem portion of an endoluminal therapeutic device. The stem portion of the therapeutic device that is mechanically engaged by the tubular collar can comprise one or more rounded members 143 that are attached to the stem portion of the therapeutic device.

The elongated pusher member is, in one presently preferred aspect, formed of an optical fiber which will bend sufficiently to follow the turns and bends of the vasculature when it is introduced, such as through a catheter, into the body. Alternatively, the elongated pusher member can be formed of suitable materials for conducting radio frequency energy, magnetic energy, or ultrasonic energy, such as an elongated metal member, for example, or of a heat pipe for conducting heat from a heat source, to cause the tubular collar to axially recover its original shape. The proximal end 138 of the tubular collar can be attached to the pusher member by a temperature resistant adhesive, such as cyanoacrylate adhesive, for example. In the unstressed state, the tubular collar will typically have a constant inner and outer diameter extending from its proximal end to its distal end.

Figure 26:
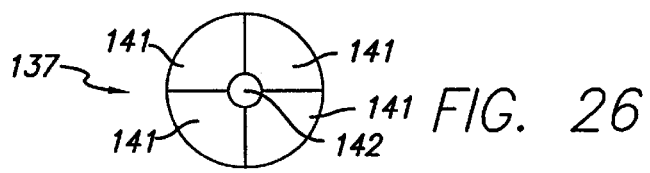
FIG. 26 is a sectional view taken along line 26—26 of FIG. 25.

FIGS. 25 and 26 illustrate the device after the tubular collar 136 of shape memory material has been heated and stressed axially, although the tubular collar can also be stressed radially, by compressing or crimping the collar over the collet to increase its length so that the distal end of the tubular collar extends beyond the distal end of the pusher, to mechanically releaseably retain the gripping arms or prongs of the collet to releaseably retain the stem 142 portion of the endoluminal therapeutic device. The stem portion of the therapeutic device that is mechanically engaged by the collet can, for example, comprise one or more rounded members 143 that are attached to the stem portion of the therapeutic device 145, such as by solder, welding or adhesive, or the like, or otherwise formed in the stem portion of the therapeutic device.

Figure 28:
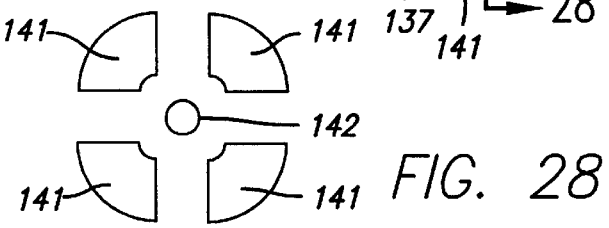
FIG. 28 is a sectional view taken along line 28—28 of FIG. 27.

FIGS. 27 and 28 illustrate the delivery system after heat has been transferred through the pusher member to the tubular collar of shape memory polymer, thereby causing it to rise in temperature above $T_g$ and axially recover to its original shape, to withdraw to release the gripping arms or prongs of the collet, to in turn release the stem portion of the endoluminal therapeutic device.

As is illustrated in FIGS. 25 and 27, the rounded members can be formed, in one presently preferred aspect of the invention, as a substantially rounded ball attached to the stem portion of the therapeutic device; or alternatively, they may be formed as one ore more substantially rounded coils of wire attached to the stem portion of the therapeutic device, which may also be a bent or looped portion of the stem portion of the therapeutic device.

In each of the foregoing embodiments, the tubular collar is preferably formed of a shape memory polymer having a glass transition temperature ($T_g$) above body temperature, such as polyurethane, heat shrink tubing such as polyethylene terephthalate (PET) or high density polyethylene (HDPE), or a shape memory metal such as nickel titanium alloy, such as that available under the trade name NITINOL, for example, that can be heat treated to have shape memory behavior. Utilizing such materials, the shape memory material has a desired stressed configuration at a temperature appropriate for introduction into the body via a catheter, and after placement, will take on a more relaxed, unstressed original shape for releasing the endoluminal therapeutic device.

From the foregoing, it will be appreciated that the endoluminal device delivery system of the invention provides a quick, safe and reliable method for delivering coils through tiny blood vessels to treat damaged vasculature. The endoluminal device delivery procedure is minimally invasive and obviates the need for surgical removal and replacement of the damaged vasculature. No penetration of cerebral tissue is needed to treat damaged vasculature using this delivery system. In addition, the coil delivery system described in the invention does not require a long surgical procedure nor any additional expensive equipment.

While a particular form of the invention has been illustrated and described, it will be apparent that various modifications can be made without departing from the spirit and scope of the invention. Thus, it is not intended that the invention be limited except by the appended claims.

What is claimed is:

1. An endoluminal device delivery system for release and deployment of an endoluminal therapeutic device through an elongated catheter within the vasculature of a patient, the endoluminal therapeutic device having a stem portion, the endoluminal device delivery system comprising:
    an elongated pusher member having a distal end;
    a body of shape memory material mounted to the distal end of the elongated pusher member, said body of shape memory material having a stressed configuration engaging the stem portion of the endoluminal therapeutic device and an axially recovered configuration withdrawn from the stem portion of the endoluminal therapeutic device; and
    a stop portion at the distal end of said elongated pusher member, said stop portion being unconnected to said body of shape memory material and said stop portion contacting the stem portion of the endoluminal therapeutic device, whereby when said body of shape memory material changes from said stressed configuration to said recovered configuration said endoluminal therapeutic device is dislodged from said body of shape memory material.

2. An endoluminal device delivery system as recited in claim 1, wherein in said stressed configuration said body of shape memory material is axially stressed to engage the stem portion of the endoluminal therapeutic device.

3. An endoluminal device delivery system as recited in claim 1, wherein in said stressed configuration said body of shape memory material is axially and radially stressed to engage the stem portion of the endoluminal therapeutic device.

4. An endoluminal device delivery system as recited in claim 1, wherein said body of shape memory material has a tubular cross-section forming a tubular collar extending from its proximal end to its distal end and said stop portion is located internally to said tubular collar for, upon shape recovery of said tubular collar, engaging said endoluminal therapeutic device to dislodge said device from said tubular collar.

5. An endoluminal device delivery system as recited in claim 1, wherein said body of shape memory material has a cross-section which is formed to accommodate said endoluminal therapeutic device.

6. An endoluminal device delivery system as recited in claim 1, wherein said body of shape memory material is comprised of a shape memory polymer.

7. An endoluminal device delivery system as recited in claim 6, wherein said body of shape memory material is comprised of polyurethane.

8. An endoluminal device delivery system as recited in claim 1, wherein said body of shape memory material is comprised of a nickel titanium alloy.

9. An endoluminal device delivery system as recited in claim 1, wherein the stem portion of the endoluminal therapeutic device includes an extension formed to engage said body of shape memory material.

10. An endoluminal device delivery system as recited in claim 1, wherein the endoluminal therapeutic device is mechanically engaged by said body of shape memory material.

11. An endoluminal device delivery system for release and deployment of an endoluminal therapeutic device through an elongated catheter within the vasculature of a patient, the endoluminal device delivery system comprising:
    an endoluminal therapeutic device having a therapeutic portion and a stem portion, said stem portion including at least one rounded member;
    an elongated pusher member having a distal end;
    a body of shape memory material mounted to the distal end of the elongated pusher member, said body of shape memory material having a stressed configuration engaging said at least one rounded member of the stem portion of the endoluminal therapeutic device and an axially recovered configuration withdrawn from said at least one rounded member of the stem portion of the endoluminal therapeutic device; and
    a stop portion at the distal end of said elongated pusher member, said stop portion being unconnected to said body of shape memory material and said stop portion contacting the stem portion of the endoluminal therapeutic device, whereby when said body of shape memory material changes from said stressed configuration to said recovered configuration said endoluminal therapeutic device is dislodged from said body of shape memory material.

12. An endoluminal device delivery system as recited in claim 11, wherein in said stressed configuration said body of shape memory material is axially stressed to engage said stem portion of the endoluminal therapeutic device.

13. An endoluminal device delivery system as recited in claim 11, wherein in said stressed configuration said body of shape memory material is axially and radially stressed to engage said stem portion of the endoluminal therapeutic device.

14. An endoluminal device delivery system as recited in claim 11, wherein said body of shape memory material has a tubular cross-section forming a tubular collar extending from its proximal end to its distal end and said stop portion is located internally to said tubular collar for, upon shape recovery of said tubular collar, engaging said endoluminal therapeutic device to dislodge said device from said tubular collar.

15. An endoluminal device delivery system as recited in claim 11, wherein said body of shape memory material has a cross-section which is formed to accommodate said endoluminal therapeutic device.

16. An endoluminal device delivery system as recited in claim 11, wherein said body of shape memory material is comprised of a shape memory polymer.

17. An endoluminal device delivery system as recited in claim 16, wherein said body of shape memory material is comprised of polyurethane.

18. An endoluminal device delivery system as recited in claim 11, wherein said body of shape memory material is comprised of a nickel titanium alloy.

19. An endoluminal device delivery system as recited in claim 11, wherein said stem portion of the endoluminal therapeutic device includes an extension formed to engage said body of shape memory material.

20. An endoluminal device delivery system as recited in claim 11, wherein the endoluminal therapeutic device is mechanically engaged by said body of shape memory material.

21. An endoluminal device delivery system as recited in claim 11, wherein said at least one rounded member comprises a substantially rounded coil of wire.

22. An endoluminal device delivery system as recited in claim 11, wherein said at least one rounded member comprises a plurality of substantially rounded coils of wire.

* * * * *

UNITED STATES PATENT AND TRADEMARK OFFICE
CERTIFICATE OF CORRECTION

PATENT NO.    : 6,296,622 B1
DATED         : October 2, 2001
INVENTOR(S)   : Daniel R. Kurz et al.

It is certified that error appears in the above-identified patent and that said Letters Patent is hereby corrected as shown below:

Title page,
Change "4,957,051" to read -- 4,957,501 --.

Column 4,
Line 47, delete "proximal".

Column 5,
Lines 15, 25, 39, 42 and 48, delete "end".
Line 52, delete "portion".

Column 6,
Line 48, delete "proximal end".
Line 50, delete "end".

Column 12,
Line 63, delete "end".

Column 14,
Line 6, delete "proximal".

Signed and Sealed this

Twenty-sixth Day of November, 2002

Attest:

Attesting Officer

JAMES E. ROGAN
Director of the United States Patent and Trademark Office